(12) United States Patent
Seppa et al.

(10) Patent No.: US 8,136,403 B2
(45) Date of Patent: Mar. 20, 2012

(54) MICROMECHANICAL SENSOR, SENSOR ARRAY AND METHOD

(75) Inventors: Heikki Seppa, Helsinki (FI); Kirsi Tappura, Tampere (FI); Jussi Tuppurainen, Lempaala (FI); Tomi Mattila, Espoo (FI); Ari Alastalo, Klaukkala (FI); Hannu Helle, Tampere (FI); Aarne Oja, Espoo (FI)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 609 days.

(21) Appl. No.: 11/988,417

(22) PCT Filed: Jul. 4, 2006

(86) PCT No.: PCT/FI2006/000240
§ 371 (c)(1),
(2), (4) Date: May 7, 2008

(87) PCT Pub. No.: WO2007/006843
PCT Pub. Date: Jan. 18, 2007

(65) Prior Publication Data
US 2009/0277271 A1 Nov. 12, 2009

(30) Foreign Application Priority Data
Jul. 8, 2005 (FI) .................................. 20050739

(51) Int. Cl.
*G01N 29/02* (2006.01)
(52) U.S. Cl. ..................... 73/627; 73/504.05
(58) Field of Classification Search ............. 73/627, 73/514.23, 514.34, 514.21, 579, 24.06, 61.75, 73/504.05
See application file for complete search history.

(56) References Cited

U.S. PATENT DOCUMENTS

| 5,323,636 A | | 6/1994 | McGowan et al. | |
|---|---|---|---|---|
| 5,536,963 A | * | 7/1996 | Polla | 257/417 |
| 5,546,946 A | * | 8/1996 | Souquet | 600/459 |
| 5,724,315 A | * | 3/1998 | Moffett et al. | 367/153 |
| 5,766,367 A | * | 6/1998 | Smith et al. | 134/2 |
| 5,867,884 A | * | 2/1999 | Rilling et al. | 29/525 |

(Continued)

FOREIGN PATENT DOCUMENTS
JP 9-230392 A 9/1997

OTHER PUBLICATIONS

Mattila, T et al: "A 12 MHz micromechanical bulk acoustic mode oscillator". Sep. 30, 2002, vol. A 101, p. 1-9.

*Primary Examiner* — J M Saint Surin
(74) *Attorney, Agent, or Firm* — Birch, Stewart, Kolasch & Birch, LLP

(57) ABSTRACT

The present invention relates to a micromechanical sensor for analyzing liquid samples and an array of such sensors. The invention also concerns a method for sensing liquid samples and the use of longitudinal bulk acoustic waves for analyzing liquid phase samples micromechanically. The sensor comprises a body and a planar wave guide portion spaced from the body. At least one electro-mechanical transducer element are used for excitation of longitudinal bulk acoustic waves to the wave guide portion in response to electrical actuation and for converting acoustic waves into electrical signals. The wave guide portion is provided with a sample-receiving zone onto which the sample can be introduced. By means of the invention, the sensitivity of micromechanical liquid sensors can be improved.

38 Claims, 8 Drawing Sheets

U.S. PATENT DOCUMENTS

| | | | |
|---|---|---|---|
| 5,914,507 A * | 6/1999 | Polla et al. | 257/254 |
| 6,215,375 B1 * | 4/2001 | Larson et al. | 333/187 |
| 6,300,706 B1 * | 10/2001 | Grudkowski et al. | 310/334 |
| 6,304,021 B1 | 10/2001 | Wolf et al. | |
| 6,474,786 B2 * | 11/2002 | Percin et al. | 347/54 |
| 6,698,283 B2 * | 3/2004 | Wado et al. | 73/204.26 |
| 6,972,423 B2 * | 12/2005 | Welland et al. | 250/573 |
| 7,199,683 B2 * | 4/2007 | Thalhammer et al. | 333/187 |
| 7,296,329 B1 * | 11/2007 | Barber et al. | 29/25.35 |
| 7,398,685 B2 * | 7/2008 | Itoh et al. | 73/599 |
| 7,555,956 B2 * | 7/2009 | Benzel et al. | 73/714 |
| 2003/0005771 A1 | 1/2003 | Percin et al. | |
| 2003/0059954 A1 | 3/2003 | Vikholm et al. | |

* cited by examiner

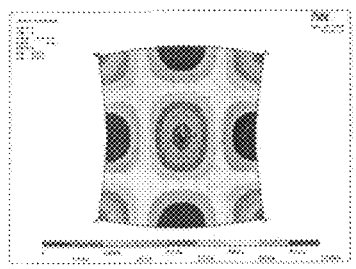 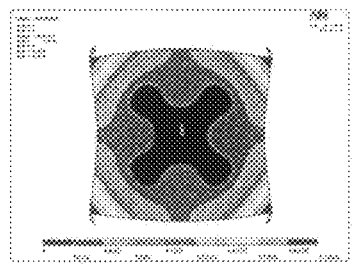 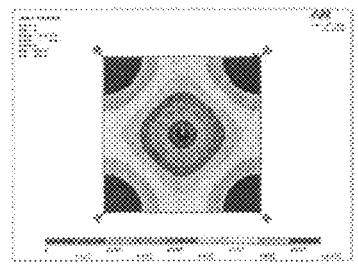
Fig. 13a　　　　　　Fig. 13b　　　　　　Fig. 13c
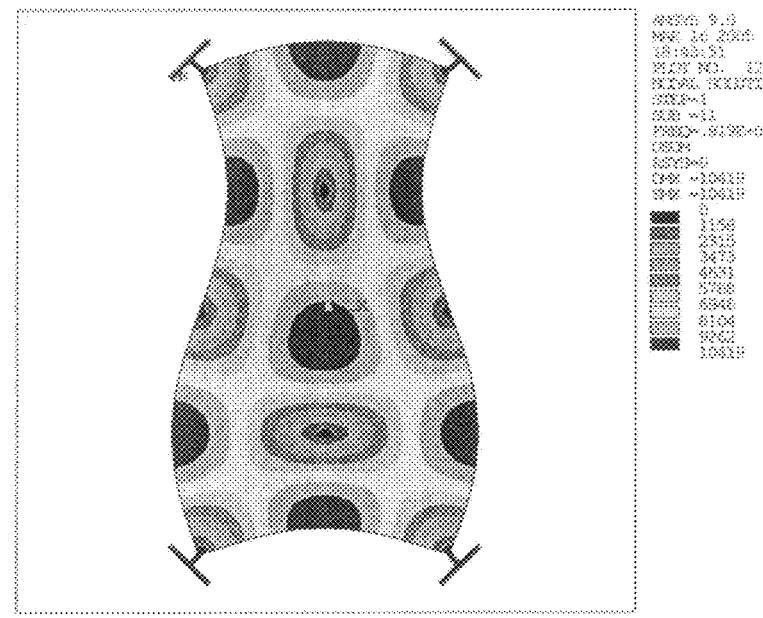
Fig. 14

MICROMECHANICAL SENSOR, SENSOR ARRAY AND METHOD

BACKGROUND OF THE INVENTION

1. Field of the Invention

The present invention relates to sensors. In particular, the present invention concerns micromechanically fabricated sensors that are manufactured on semiconductor substrates. Such sensors can be used for analyzing, for example, small amounts of biological matter. The invention also concerns a method for analyzing liquid phase samples micromechanically.

2. Description of Related Art

Using modern silicon micromachining techniques, it is possible to batch-fabricate micromechanical devices suitable for sensor applications. Many of these devices take advantage of silicon-on-insulator (SOI) structures. The recent research related to molecule-specific membranes [Vikholm1-4] has expanded the possibilities of micromechanically implemented biochemical analysis. It is well known that the biochemical analysis can be made by using micromechanical resonators, whose resonant frequency is altered by changes on the surface mass of the sensor. By monitoring the resonant frequency, information on the substance on the sensor is obtained.

In general, the resolution of detecting a small change in mass is inversely proportional to the effective mass of the resonator and directly proportional to the resonant frequency and the Q-value of the resonator. In addition, the resolution is proportional to the displacement amplitude of the resonator. Thus, the higher the mechanical energy stored by the resonator the better the resolution.

Surface wave sensors are based on exciting surface acoustic waves (SAWs) to the substrate. In such sensors, the wave propagates on (or in the vicinity of) the surface of the sensor, making them sensitive to small changes of mass on the surface of the sensor, for example, mass growth in gas environment. The SAW devices usually oscillate either in vertical or horizontal direction transverse to the propagation direction of the waves. The displacement of the surface of vertical mode SAW sensors is big, which makes them less suitable for analyzing of liquid samples. In particular, detection of small mass changes is difficult from liquid samples. This is because the oscillations are easily damped due to the vibrational energy radiated/lost to the liquid. Shear-Horizontal SAW (SH-SAW) sensors have been utilized as liquid phase sensors, though, as they utilize parallel-to-surface transverse waves. A SAW silicon micromechanical resonator utilizing a flexural wave mode can also be used but it is also suitable only for gas phase analysis.

Bulk Acoustic Waves (BAWs) propagate in the whole volume of the resonator. Thickness Shear Mode BAW Resonators (TSMs), which utilize transverse waves between the sensor electrodes, are well suited for gas analysis. They can also be used also for liquid phase analysis to some extent. Shear-Horizontal Acoustic Plate Mode Sensors (SH-APM) are more mass sensitive than TSMs but still much less sensitive than SAW devices. One principal reason for that is that the energy density on the surface of BAW sensors is lower than in SAW devices.

Almost any mechanical resonator can successfully be applied for measuring mass growth on the surface if placed in gas. When analyzing liquid samples, two problems arise. First, only sealed structures can be used. That is, the liquid-receiving section of the sensor has to be mechanically isolated from the other parts of the structure, such as transducer elements. Second, mechanical oscillations will be heavily damped by dissipations related to the liquid sample. Such dissipations result, for example, from relatively high masses of liquid-phase samples and viscous properties of the liquid, as well as from the relatively similar acoustic impedances of resonator materials and the liquid (typically within a decade). Thus, a significant amount of acoustic energy can be transmitted (lost) through the solid-liquid interface. This is why almost only sensors based on TSM, SH-APM, and SH-SAW, which all generate waves that propagate primarily in the shear horizontal (transverse, parallel-to-surface) direction, have been used as biosensors. However, the sensitivity and usability of the devices is not sufficient to meet the requirements of modern liquid phase analysis applications. A further disadvantage of prior art BAW devices is that the thickness of the resonator is dictated by the desired operational frequency.

SUMMARY OF THE INVENTION

It is an aim of the present invention to eliminate at least some of the problems of the prior art and to provide a novel micromechanical BAW sensor suitable for liquid phase analysis.

It is also an aim of the invention to provide micromechanical BAW sensor array suitable for parallel analysis of several samples.

It is another aim of the invention to provide a novel method for analyzing small amounts of liquid phase samples micromechanically and a novel use of longitudinal bulk acoustic waves.

The invention is based on the idea of using longitudinal bulk acoustic waves for detecting phenomena occurring in a sample, especially a liquid phase sample, by micromechanical arrangement.

A sensor according to the invention is manufactured on a substrate (body) and it exhibits a wave guide portion for carrying the acoustic waves. The wave guide portion is located at a distance from the body. The wave guide portion is also provided with a sample-receiving area on at least one of its surfaces. The longitudinal bulk acoustic waves are produced by at least one electro-mechanical transducer element located in the vicinity of the wave guide portion.

The method according to the invention comprises the steps of introducing a liquid sample on a sample-receiving area of a micromechanical wave guide and transmitting longitudinal bulk acoustic waves into the wave guide using an electro-mechanical coupling, and converting the acoustic waves into electrical signals for sensing the impact of the sample on the vibrational behaviour of the wave guide.

A sensor or multiple sensors according to the invention can be incorporated into an array of several micromechanical acoustic sensor elements.

More specifically, the invention is characterized by what is stated in the characterizing part of claim 1.

The sensor array is mainly characterized by what is stated in the characterizing part of claim 29.

The method array is characterized by what is stated in claim 34.

The use is characterized in claim 38.

Considerable advantages are obtained by means of the embodiments of the invention. Thus, the surface-normal component of displacement remains minor as a result of the bulk wave propagating in longitudinal direction. The contraction and expansion caused by the Poisson's effect in the vertical (perpendicular-to-surface) direction remains small. The surface-normal component of displacement can be made extremely small by appropriate cutting of the single crystal silicon. In addition, by applying such a lateral acoustic mode that exhibits contraction in one of the parallel-to-surface directions while expanding in the other, the surface-normal component of displacement is expected to be reduced even further, and thus also the losses due to acoustic radiation to the liquid.

A typical SOI-device layer thickness in the order of 10-30 μm makes the bulk acoustic wave propagation suitably sensitive to any changes in the physical properties of the sample-receiving area. In particular, if the sample-receiving area is provided with a molecule-specific layer (MSL), the alterations in the properties of the MSL are easily detectable. On the other hand, the structure is thick enough to contain sufficient energy in contrast to the surface acoustic wave (SAW) devices where excessive damping can occur due to the inevitable viscous loading by the liquid.

In addition, strong coupling can be achieved between the electrical and acoustic energy because of the use of longitudinal waves. The electro-mechanical conversion can be realized, for example, by using narrow-gap capacitive transducers, piezoelectric transducers, magnetic transducers or thermal transducers. A standing-wave operation (resonance) can be utilized in the device for improved coupling and resolution.

Thus, we have found that length-extensional (longitudinal) bulk acoustic waves actuated into a micromechanical device are well suited for analysis of liquid samples. In particular, by utilizing an additional layer with a facility for specific binding of molecules (antigens, antibodies, DNA etc.), cells, even tissue containing samples etc., an effective biosensor can be achieved. Examples of areas of potential use of such a sensor are analyses for clinical, environmental and research purposes in the fields of biology, biotechnology, chemistry and health-care, for example. Especially in immunology advances in liquid phase analysis methods are welcomed, as well as in other routine bioanalyses.

The longitudinal-wave sensors can be economically manufactured from silicon-based wafers. Moreover, micromechanical silicon-based components provide intrinsic potential for batch-fabricated sensor devices—including sensor arrays or matrices—with integrated readout electronics. Silicon-based sensors and the readout and actuation electronics could, in principle, be incorporated into any common integrated circuit (IC) structure. Sensors for different chemical and biological analysis can be implemented by applying different molecule-specific membranes (with low non-specific binding). Non-specific binding, temperature compensation and other interference phenomena can be eliminated by using integrated reference devices.

According to a preferred embodiment, at least the sample-receiving zone of the resonator is open to the exteriors of the device. Either an open front side of the resonator (wave guide portion) or a back side of the resonator in the interior of the device can be used for receiving the sample, depending on the embodiment. By an "open" structure, we mean such a solution, where the sample can be introduced to the sample-receiving zone directly, or through an opening in the device. The sensor or a plurality of sensors can be packed in a housing having a sealed portion or a plurality of such portions, which can be penetrated for sample introduction. The housing can be, for example, a ceramic or plastic casing typically used in semiconductor industry.

From the practical point of view, the described structures allow
   isolation of the liquid sample from the open structures required for capacitive electro-mechanical coupling,
   easy liquid sample insertion,
   easy preparation of the molecule-specific surfaces and associated buffer layers (e.g. gold),
   the device to be manufactured using batch-fabrication methods available in industry,
   critical parts of the device to be hermetically or vacuum encapsulated using existing industrial methods.

The sensor can be used in various branches of industry and business. Examples of potential application areas of the embodiments of the invention include:
   medical diagnostic: e.g. rapid diagnostics tests at doctors office,
   home tests (welfare, diagnostics),
   tests for screening drugs of abuse and doping,
   detection of chemical and biological weapons and explosives,
   environmental monitoring,
   monitoring of industrial processes,
   detection of flavour compounds,
   drug development, and
   research.

Although the described resonator structure is especially designed for liquid samples, it is also expected to give excellent results when studying gas phase samples.

The term "longitudinal" is used for describing the direction parallel to the propagation direction of the acoustic waves.

The term "lateral" is used for describing the directions parallel to the sample-receiving surface of the wave guide.

By the terms "planar wave guide portion" and "planar resonator", we mean a thin (laminar) structure capable of carrying bulk acoustic waves actuated and sensed by the transducer elements located essentially in the vicinity of the fringe area (lateral sides) of the resonator. However, the resonator does not have to be uniformly even, but can have a variable thickness and/or sample-receiving surface geometry.

Next, the invention will be examined more closely with the aid of a detailed description and with reference to the attached drawings.

BRIEF DESCRIPTION OF THE DRAWINGS

FIGS. 13a-13c shows three different simulated mode structures (oscillation amplitudes) of a square-shaped resonator, FIG. 14 shows an exemplary simulated mode structure (oscillation amplitude) of an elongated resonator.

DETAILED DESCRIPTION OF THE INVENTION

According to a preferred embodiment, the sensor is manufactured from a semiconductor-on-insulator, preferably a silicon-on-insulator (SOI) wafer. The body of the wafer is also preferably made of a semiconductor material, such as silicon, but also other materials, such as glass or other insulators, can be used. By using such a semiconductor-based structure, the advantages of modern micromachining techniques can be taken advantage of. In particular, such a structure offers low source material and manufacturing costs. The crystal (lattice) structure of the semiconductor layer forming the device layer of the wafer has to be such that it can carry longitudinal acoustic waves. A lattice structure and cutting of crystal resulting in isotropic or anisotropic propagation of waves in the two lateral directions can also be used.

The number of transducers may vary, for example, from 1 to 4. That is, the same transducer can be used for both transmitting and receiving the acoustic signals or separate transmitters and receivers can be used. In a typical embodiment, the device comprises two or four transducers placed, for example, on each end of a rectangular resonator.

Figure 1:
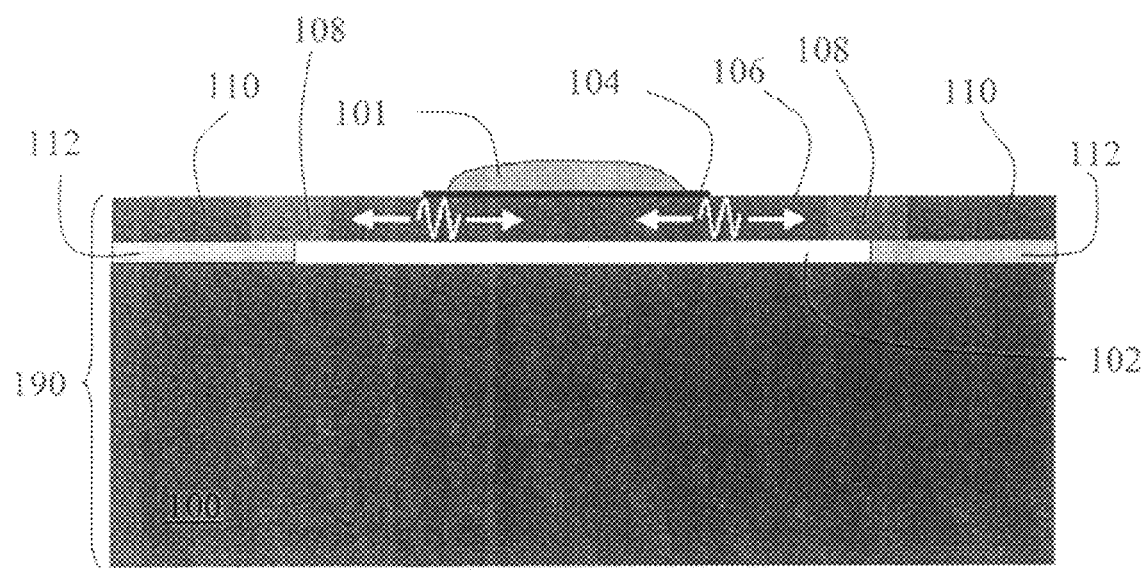
FIG. 1 shows a cross-sectional side view of a sensor according to an embodiment of the invention.

FIG. 1 illustrates schematically a structure of a first embodiment of the sensor. The sensor device is manufactured on a semiconductor body 100. Electric electrodes 110 forming a part of the transducer elements of the device are separated from the body 100 by insulator layers 112. In this example, the longitudinal bulk acoustic wave is generated and detected using electromechanical piezoactive transducers 108 coupled between the electrodes 110 and a wave guide 106. The wave guide 106 and the electrodes 110 are formed by a released section in the device layer of a silicon-on-insulator (SOI) wafer 190. The spacing between the wave guide 106 and the body 100 is denoted with a reference number 102.

A molecule specific layer (MSL) 104 can be deposited on top of the wave guide. If the liquid sample 101 contains molecules matching the MSL, the physical properties of the MSL change, which causes a detectable change in the bulk acoustic wave propagation. Both the speed and dissipation of the wave can be affected by a change of the surface layer. Generally, the speed can be detected by detecting the resonant frequency and the dissipations via the Q-value of the resonator.

Typically an MSL layer comprises a ground matrix having a capacity for preventing non-specific binding. Such a layer can comprise hydrophilic polymer covalently bound to a buffer layer (e.g. of gold through sulphur bonds) and partly embedded specific (bio)molecules. The specific molecules have to be at least partly situated on the sample-receiving surface of the MSL layer. The specific molecules are typically antibodies or their Fab-fragments. Also the specific molecules can be bound to the subbing layer covalently. The thickness of such an MSL coating is typically only 4-10 nm.

According to one embodiment, also the specific parts of the MSL are synthetically prepared (molecular imprinted polymers).

Application of the MSL on the sample-receiving surface of the resonator can be carried out in a process step closely related to the manufacturing of the device, for example, by SOI-technology. As the sensor device itself is very generic, the MSL can also be applied in a unit process. Thus, sensors can be manufactured without knowing the special applications of the end users. As the sample-receiving zone of the resonator is preferably open to the exterior, the MSL coating can be applied with a suitable apparatus on the sensor directly to the resonator or through openings in the sensor structure. If the sensor is tightly encased, the MSL is preferably applied before the sealing of the casing. The buffer layer can also be applied in the manufacturing phase of the device or in a later phase.

The body 100 and the device layer of the wafer are preferably made of Silicon (Si), but also other semiconductor (and the like) materials, such as Germanium (Ge), Gallium-Arsenide (GaAs), diamond and sapphire can be considered is some applications. In particular, silicon carbide (SiC) may be applicable for some purposes, maintaining some of the benefits of Silicon, namely good processability and IC-compatibility. The body and the device layer can also be of different materials. In general, beneficial properties of the wave guide material (the device layer) are low internal losses (high Q), high Young's modulus, and good thermal properties. If capacitive actuation is used, the device layer should also have high conductivity. Another property of the device layer that can be taken advantage of is the lattice order, especially the anisotropic elastic properties resulting from the lattice structure (e.g. Si). The semiconductor layer can also be doped, for example, to increase its conductivity. The insulator layer can be a buried oxide (BOX) layer formed of, for example, quartz ($SiO_2$).

Figure 2:
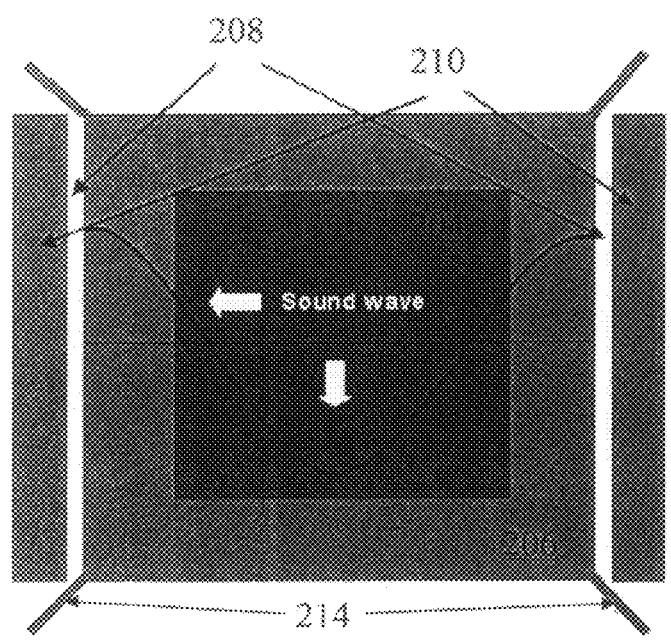
FIG. 2 illustrates a lateral view of a sensor according to an embodiment of the invention.

In FIG. 2, the structure of FIG. 1 is illustrated using a top view. In this example, the wave guide portion 206 is rectangular, enabling equal standing sound waves to be carried in both lateral directions (white arrows, only one pair of electrodes shown). In standing wave (resonance) condition, the length of the resonator plate is such, that it equals a half of the wave length λ (or its multiple) of the desired acoustic frequency in the medium of the wave guide. The MSL is denoted with a reference number 204. FIG. 2 also depicts mechanical supports 214, which can be attached for example to each corner of the wave guide portion 206. The supports 214 are preferably such that they do not significantly interact with the propagating wave. Alternatively to in-layer supports 214, also insulator supports can be used. These types of supports are illustrated in the context of forthcoming embodiments referring to FIGS. 4, 5, 8 and 9.

Acoustic frequencies are typically in the range of 2-20 MHz, preferably 5-15 MHz, depending on the amount and properties (especially the viscous properties) of the sample and the properties of the sensor device. Depending on the material of the wave guide portion, this results in acoustic wavelengths of 200-9000 μm, typically 400-4000 μm.

Typical in-plane dimensions of the wave guide portion are 600-1200 μm (longitudinal)×400-900 μm (transverse) in one-dimensional modes of operation and 600-900 μm for both lateral directions in two-dimensional modes of operation. The thickness of the wave guide portion can be, for example 10-30 μm. The lateral dimensions of the wave guide portion are adjusted taking into account the used BAW wavelength and desired vibrational modes.

Figure 4:
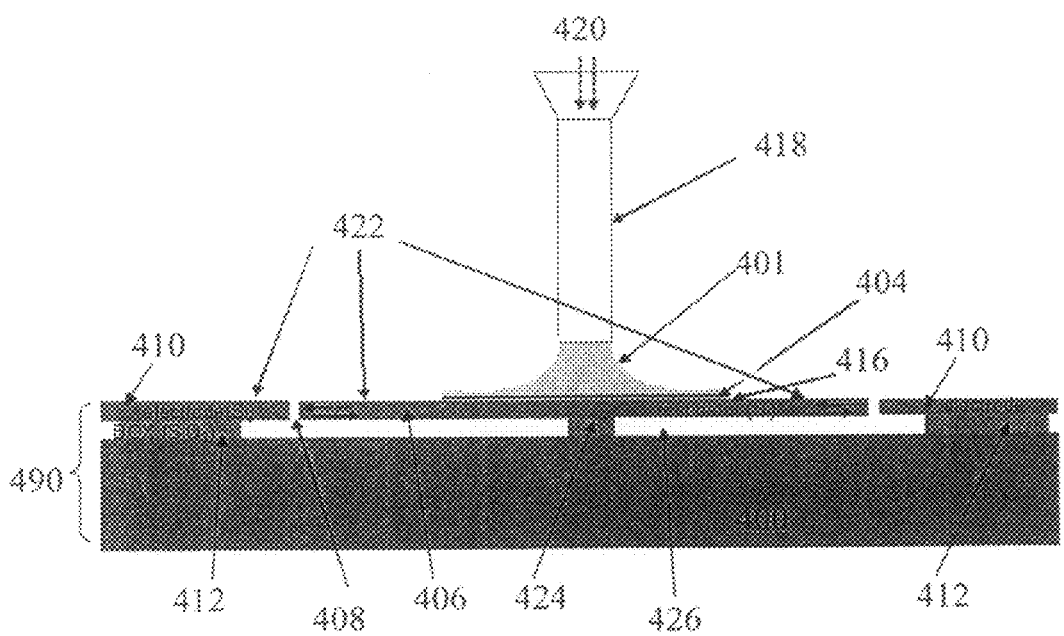
FIG. 4 depicts a cross-sectional side view of a sensor having a capillary sample injection tube.

The electro-mechanical conversion of energy can be carried out capacitively, as shown in FIG. 4. In such embodiment, the transducer electrodes 410 are separated from the wave guide 406 by narrow gaps 408. The size of the gaps 408 is typically 0.7-1 μm, preferably 0.3-0.7 μm. Narrower gaps provides for better capacitive coupling of the transducers to the wave guide.

Considering the introduction of a liquid sample, the embodiment of FIG. 4 represents an open system, where the sample-receiving surface is directly accessible, as was also the case in the embodiment of FIG. 1.

FIG. 4 illustrates also an embodiment, where the sample-receiving surface of the wave guide is coated with hydrophobic material 422 outside the actual sample-receiving zone 404. In a preferred embodiment, also the electrodes 410 and/or the narrow gaps 408 are coated with hydrophobic material 422. The hydrophobic coatings 422 enable easy sample introduction using an injection tube 418. The sample spreads over the sample-receiving zone 404 but when close to the borders of the zone, the hydrophobic coating 422 prevents the sample from entering outside the sample-receiving zone, and ultimately into the capacitive gaps 408 or electrodes 410. The liquid sample can be directed to the sample-receiving area through narrow bores e.g. laser drilled bores in the device package (e.g. LTCC or plastic). In one embodiment, the sample-receiving zone, typically the MSL on the zone, 404 can be made hydrophilic to achieve or to assist concentration of the sample on the desired measurement area.

An additional buffer layer or layers 416 can be arranged on the resonator. In a preferred embodiment, a buffer layer is applied between the resonator and an MSL. The buffer layer is preferably made of an inert substance, such as gold. By the buffer layer, a suitable basis for the MSL can be formed. Also the total mass or resonance properties of the resonator can be affected by the buffer layer.

The wave guide portion 406 can be separated (spaced) from the body 400 of the device by using the insulator layer of the SOI wafer. In the embodiment of FIG. 4, a support 424 is left in the centre of the wave guide 406. The support can be point-like or elongated in the direction perpendicular to the projection plane of FIG. 4. In another embodiment, there are two or more supports 424 placed symmetrically with respect to the resonator 406, preferably at the node points of the acoustic waves or at points at a distance of $\lambda/4+N*\lambda/2$ from the ends of the wave guide, where N=0, 1, 2, 3, . . . .

The sample can be carried to the sensing surface 404 by a separate capillary pipe 418 or bore included in the package of the chip manufactured e.g. by hot-embossing, injection molding, alumina plate or LTCC technology. The end of the pipe 418 is attached close to (above) the sensing surface 404 so that the sample droplet can stay in touch with pipe while the lower part of the droplet is touching/spreading over the hydrophilic sensing surface.

According to one embodiment, shallow cups or basins are etched on the resonator plate (especially on the sample-receiving zone) to ease liquid handling and to improve the alignment of the liquid sample with the mode structure of the resonator. This kind of local thinning of the plate can also be used to enhance the mass sensitivity of the sensor, while still providing the possibility to use structures thick enough to resist bending (induced e.g. by undesired capillary forces possibly occurring in packaged systems).

Especially in open systems that may be relevant to some applications, the noise generated by the evaporation of small-volume liquid samples (causing fluctuations in the size of the droplet) can be a problem. Such noise can be minimized/eliminated by careful design of the resonance mode, i.e. by selecting the lowest harmonic resonance mode that allows placing the edges of the droplet on/close to the nodes of the standing wave on the resonator.

Structures based either on one- or two-dimensional longitudinal BAWs can be used in all of the described embodiments. If a two-dimensional BAW arrangement is desired, each transducer element can extend to the vicinity of two adjacent ends of the resonator. Alternatively, there may be manufactured two pairs of transducer elements, one for each perpendicular lateral direction. However, different two-dimensional modes can also be excited with a single transducer element, the modes depending on the crystal orientations and the lateral dimensions of the plate.

Figure 5:
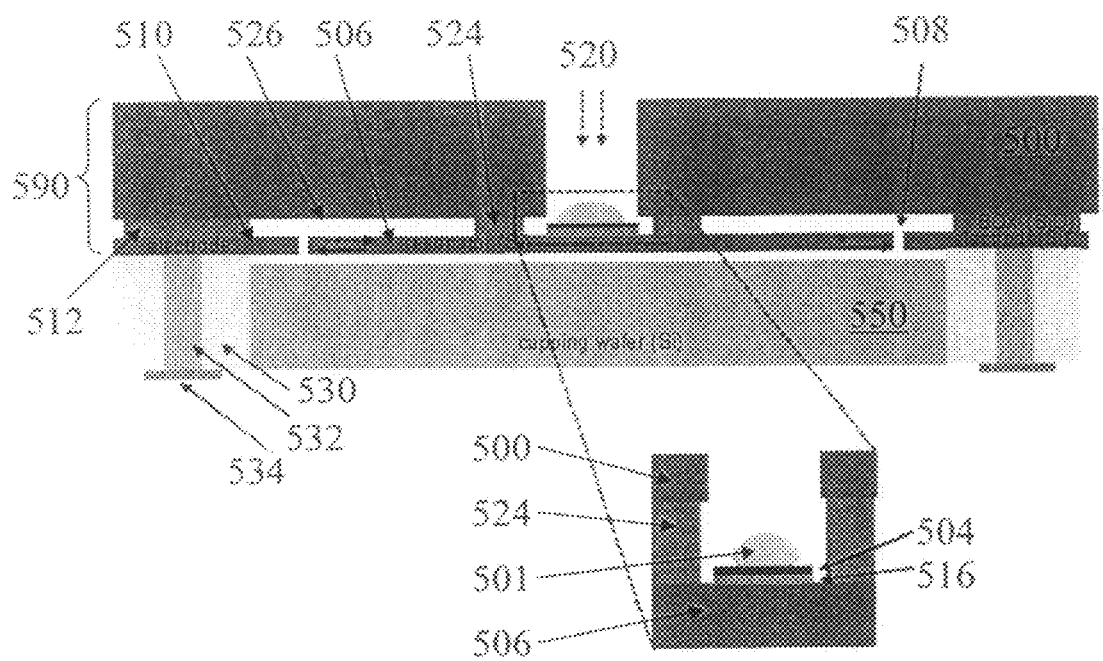
FIG. 5 depicts a cross-sectional side view of a sensor having a modified base layer for sample injection.
Figure 8:
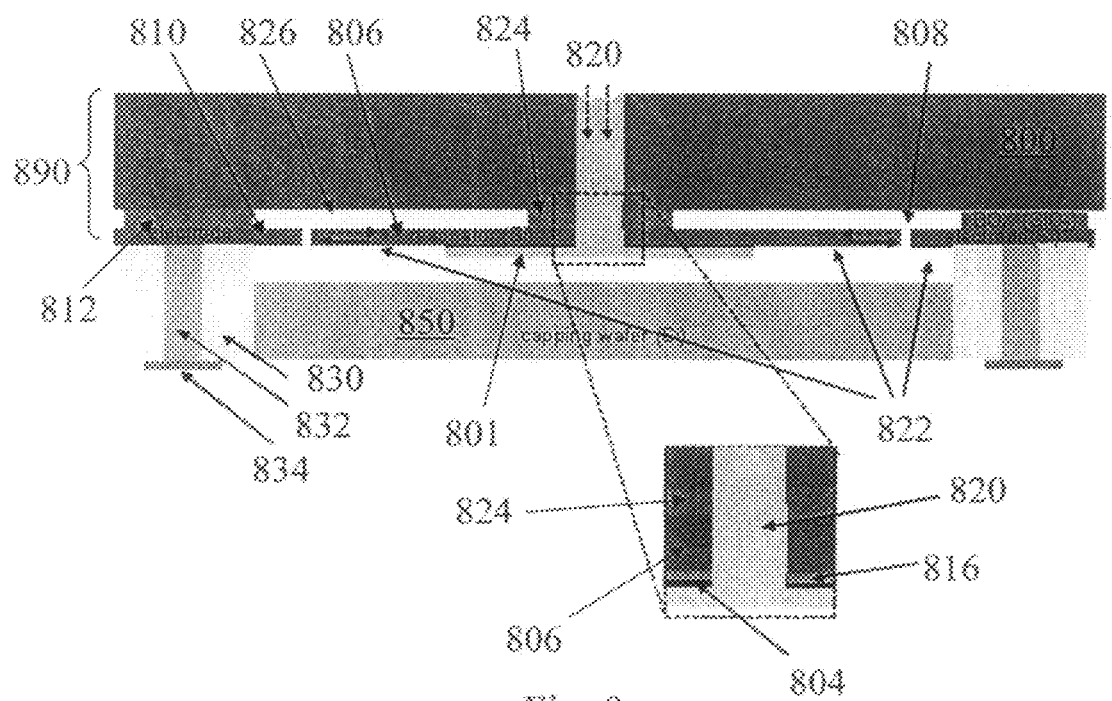
FIG. 8 depicts a cross-sectional side view of a sensor according to another embodiment of the invention.
Figure 9:
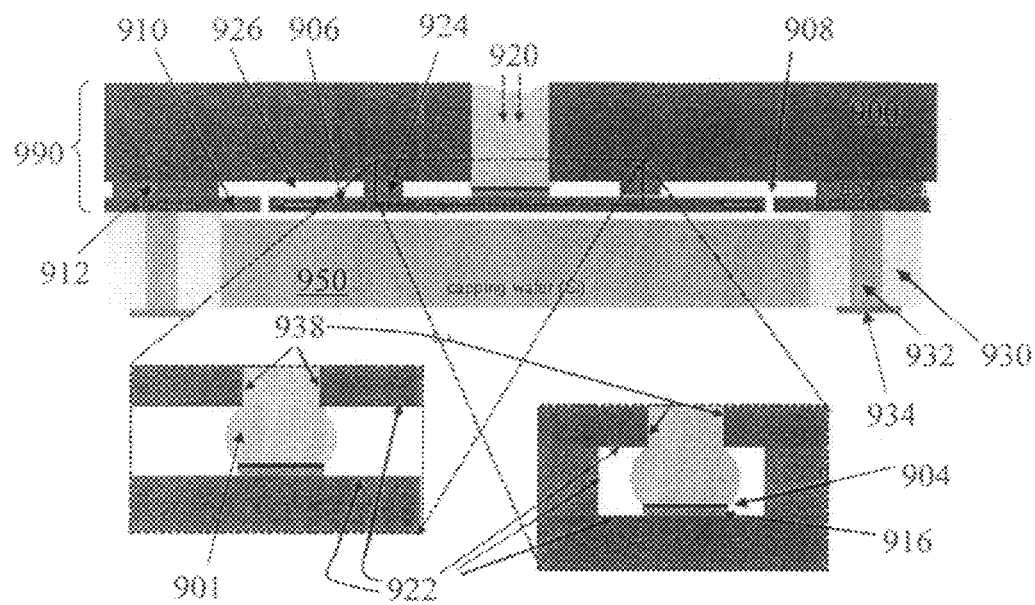
FIG. 9 depicts a cross-sectional side view of a sensor according to yet another embodiment of the invention.

FIGS. 5, 8 and 9 illustrate embodiments, where the sample is introduced through the body 500, 800, 900 of the device, respectively.

Figure 6:
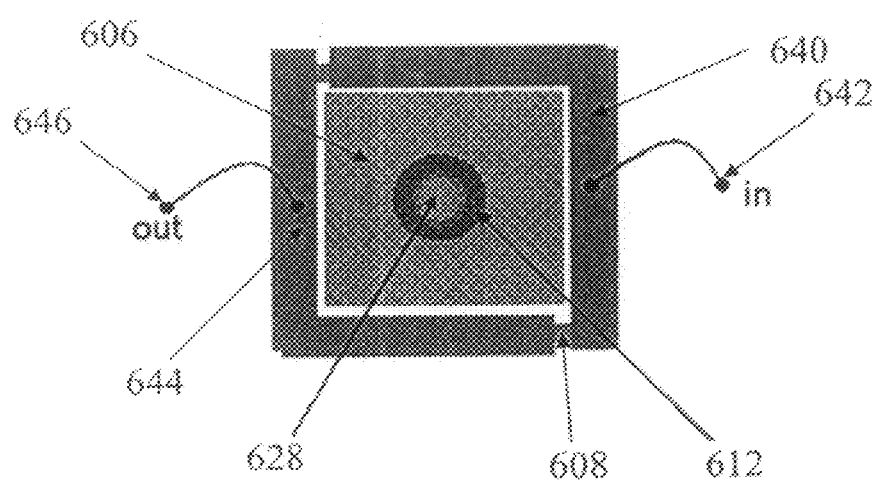
FIG. 6 shows a lateral view of a sensor kernel according to an embodiment of the invention.

The embodiment shown in FIGS. 5 and 6 in two different angles represents a 2D-BAW structure with square-extensional lateral vibration mode. The resonator 506, 606 is made on a silicon-on-insulator (SOI) wafer using standard processing methods [Mattilal, Kaajakaril]. The resonator 506, 606 is anchored to the body 500 at center. Additional or substitutive corner anchoring is also possible. The buried oxide (BOX) anchor 524 is ring-shaped (a torus) and accommodates the sample-receiving surface 504 at the center. The sensing surface is accessed from "backside" of the device via an opening 520 etched through the substrate 500. The ring-shaped oxide anchor 524 physically isolates the two sides of the SOI-wafer. This allows easy sample insertion since the liquid is separated from the open structures in device layer, especially the electromechanical coupling gaps and isolation trenches etc.

Because the device-layer and substrate sides of the wafer are isolated, hermetic wafer-capping of the device-layer side are also easily obtained. If necessary, vacuum encapsulation can be applied for increased resonator Q-value. The final packaged structure conveniently allows the sample insertion and electrical contacting from opposite sides of the component. The electrical contact pads are denoted with a reference numeral 534, the contacting feed-throughs, preferably also of silicon, being denoted with a numeral 532. The feed-throughs 532 can be isolated from the capping wafer 550 with isolators 530.

In the embodiments where the sensing surface is at the centre of the resonating plate, the coupling to the laterally propagating sound waves is strong for the molecule specific layers exhibiting sufficient amount of stiffness. This is because the largest strain, i.e. relative displacement of the lattice planes, surrounds the centre. From another perspective, the resonator motion in absolute coordinates is smallest near the centre which prevents unwanted changes in the effective mass of the resonator due to the mass of the liquid sample. The molecular recognition taking place at the sample-receiving surface, preferably the molecule-specific layer, affects the sound propagation which is detected as a change in the resonance frequency. The ring-anchor diameter (analysis surface area) can be somewhat varied to meet the resolution or other requirements (e.g. sample size). However, increasing the anchor size will result in decrease of the resonator Q-value. If necessary, a higher-order mode, such as a "$\lambda/4-\lambda-\lambda 4$" mode (see e.g. FIG. 10), which allows anchor positioning at the node points can be utilized. In addition to the square extensional mode, other modes of the square plate may also be utilized if anchor positioning closer to the node points is required (see e.g. FIG. 7).

Figure 7:
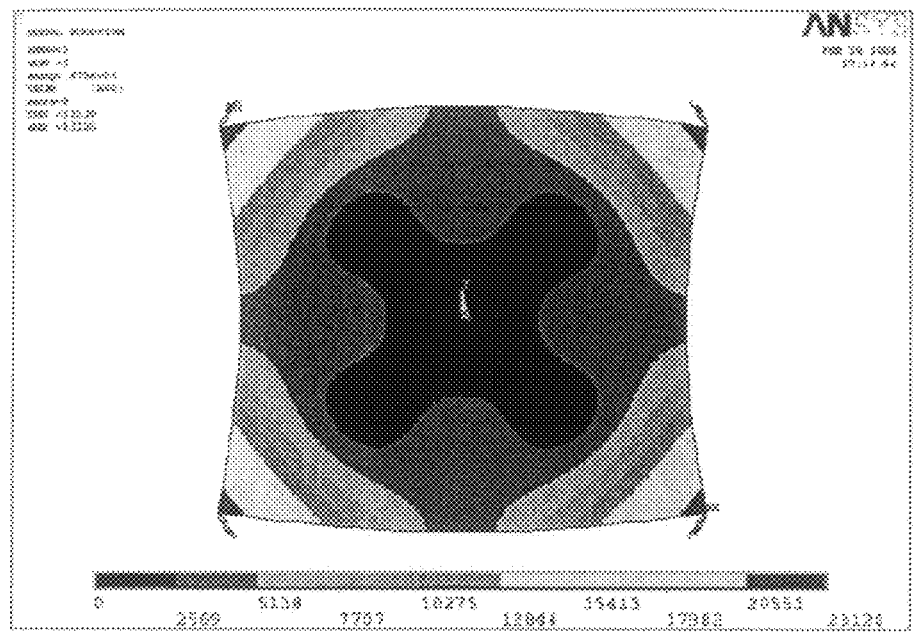
FIG. 7 shows simulation data obtained by exciting an acoustic mode exhibiting five different node position close to the center area of the resonator.

In FIG. 7 an example of the total vibrations of a simulated mode is shown. From the figure it is seen that the illustrated mode exhibits very little motion on the five spot-like areas (merged with each other to form an x-shaped pattern in the figure due to the poor color scale resolution) which can be used as potential anchor positions (i.e. anchors attached to those positions do not generate significant losses to the mode).

More simulated oscillation mode structures are shown in FIGS. 13-16. In the figures, the amplitude of the vibrational movement of the resonator plate is illustrated by using shading. The shades on the left of the shade bars shown represent low amplitudes and the shades on the right end of the bars represent higher amplitudes. The minimum and maximum values are indicated in the figures.

In FIGS. 13a-13c, the total vibrations of three low modes (i.e., Lame, "Corner-Lame" and Square-Extensional modes) of a square-shaped resonator are shown. Although being highly two-dimensional due to the dimensions of the resonator, all the shown modes can be excited by actuation from one side of the resonator only. This illustrates the advantage of the use of longitudinal BAW modes, that the waves are easily reflected from the boundaries of the resonator, which provides for high flexibility in selecting the mode used. Of course, diverse modes can be excited by using a more complex excitation scheme (more electrodes, different dimensions, differently placed anchor parts).

FIG. 14 shows the total vibrations of a preferred mode excited to an elongated resonator. The surface-normal component of the vibration is very low on the whole area of the resonator.

Figure 15A:
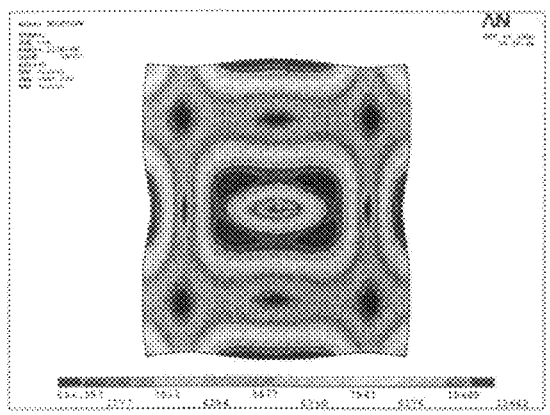
FIGS. 15a and 15b show total and surface-normal oscillations, respectively, of another mode excited to a rectangular resonator.
Figure 15B:
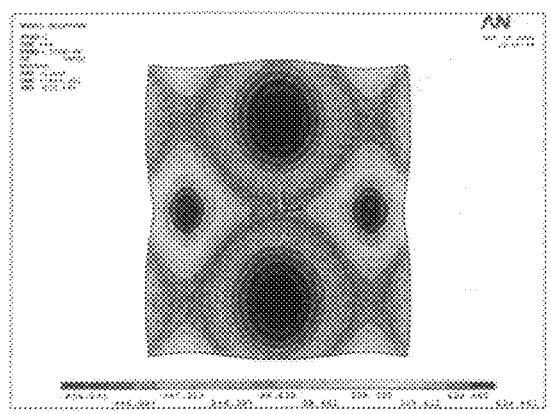

FIGS. 15a and 15b show a total and surface-normal amplitudes, respectively, of another preferred mode structure of a resonator. The shown mode can be used for effectively analyzing the areas close to the centre of a sample droplet, as the lateral oscillation energy is high and surface-normal oscillation energy is low in a ring-shaped area in the vicinity of the centre of the resonator. In addition, all the movements are relatively low outside the ring-shaped area, where the boundary of the droplet is placed. This configuration enables the reduction of the noise generated by possible (undesired) variations in the size of the droplet.

Figure 16A:
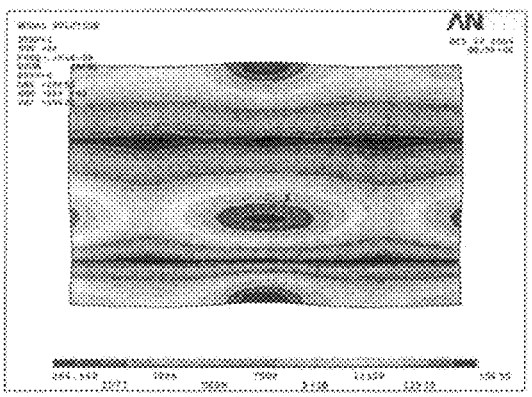
FIGS. 16a and 16b show total and surface-normal oscillations, respectively, of yet another mode excited to a rectangular resonator.
Figure 16B:
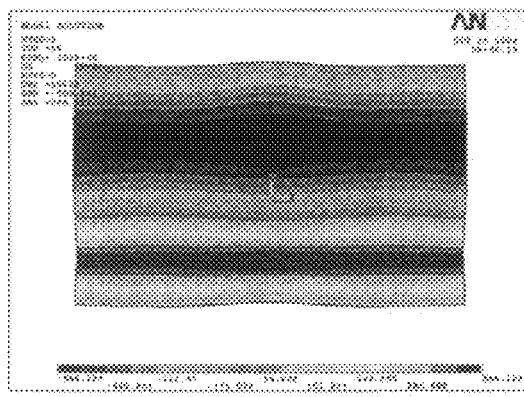

FIGS. 16a and 16b show a total and surface-normal amplitudes, respectively, of another mode structure of a resonator.

Referring now back to FIG. 8, which illustrates an embodiment, where the sample is introduced through the body 800, but still the front side of the device layer of the structure is used for analysis. In the embodiment, the semiconductor body 800 and the resonator 806 are provided with openings for introduction of samples on the sample-receiving zone from the direction of the semiconductor body 800. Thus, the basic structure of the resonator is as described referring to FIG. 4, but a hole 820 etched through the substrate 800 now continues through the whole structure. The liquid samples, as well as the solutions needed for the preparation of the molecule-specific coatings 804 of the sample-receiving zone, are dispensed in the hydrophilic (capillary) opening 820 from the substrate side. The opening 820 leads the liquid to the front side of the structure where the central area of the resonator 806 is made hydrophilic, while the rest of the surfaces are made hydrophobic. Both gravitational and capillary forces can be utilized for the transport of the liquid. If seen beneficial, additional under- or overpressure may also be applied, as well as protective wafer capping 850 on the device-layer side. The end of the hole 820 on the substrate side can even be plugged and the device-layer side hermetically capped (or vacuum encapsulated) after the preparation of the device and the molecule-specific membrane 804. The plug is broken while injecting the sample. If the interiors of the device are vacuum encapsulated, the prevailing underpressure helps to transport the sample onto the sample-receiving zone. The support 824 can be ring-shaped as described above. Appropriate hydrophilic or hydrophobic coatings can be arranged on the support and surrounding surfaces in each case for assisting transporting of the sample in contact with the resonator.

Figure 10:
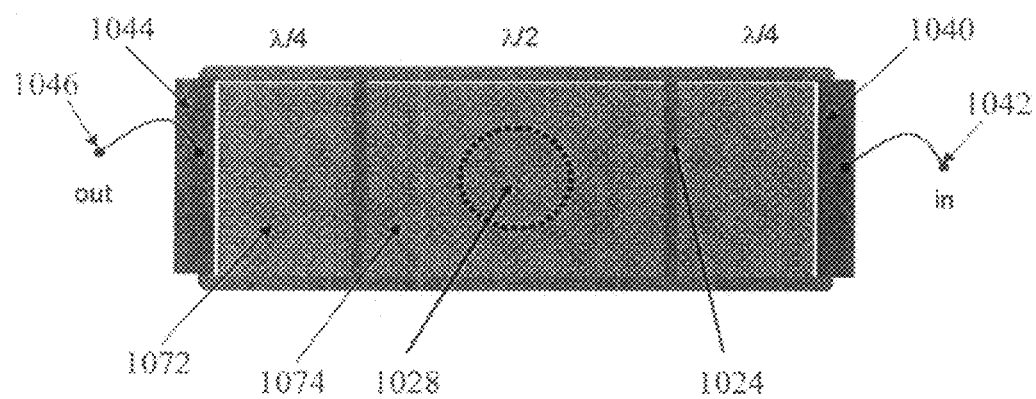
FIG. 10 shows a lateral view of a sensor kernel according to another embodiment of the invention.

FIGS. 9 and 10 show yet another embodiment of the device. The device represents a one-dimensional wave version of the device shown in FIG. 6. Thus, the wave guide 906 acts as a 1D-BAW resonator vibrating in a lateral length-extensional mode. The resonator 906 consists of two arm-plates 1072 (having a preferable length of $\lambda/4$), connected to each other by a bridge-plate 1074 (preferably of $\lambda/2$ (or $n*\lambda/2$) in length) on which the molecule-specific coating 904 is attached with the required buffer layers 916 (e.g. gold). As in the case in 2D-BAW, the sensing surface 904 on the backside of the device layer can be accessed from the backside via a hole (or holes) etched through the substrate. However, now the two oxide ridges 924, 1024 at the node points protect the open structures of the device-layer side only in one dimension. Hydrophobic surface treatments can be used to concentrate the liquid to the hydrophilic sensing surface on the centre of the bridge-plate also in the other lateral direction. Similar hydrophobic/hydrophilic treatments can also be applied if the open front side of the resonator is used for sensing in either 1D- or 2D-BAW resonators, as in previous embodiments.

In both of the 1D and 2D approaches where the backside of the device layer is applied for sensing, the molecule-specific membrane, possible buffer layers underneath (e.g. gold) and possible surface treatments to make surfaces hydrophilic/hydrophobic can be conveniently deposited through the hole in the substrate. The substrate acts as a self-aligned mask. In the case of front side detection, additional masks are needed for the surface treatments.

As described above, the sensor can be designed to be driven in a 1D or 2D mode. 2D operation provides several advantages that result in better signal quality, that is, resolution of experiments. First, by using crosswise oscillations, the energy-storing capacity of the wave guide can be better exploited. The wave guide can thus be kept thin for improved sensitivity. Second, 2D arrangement provides more possibilities for selecting the operational wave mode. By a carefully selected mode, the normal-to-surface motion of the crystal can be reduced. This is because when using a mode where while the resonator is expanding in one cartesian direction, it contracts in the other, the displacements in the third cartesian direction can be minimized.

The quality factor Q of an unloaded resonator can be as good as 80 000-200 000, preferably at least 120 000 and even higher, when operating at a frequency of 10 MHz in vacuum.

The area of the sample-receiving zone can be 5-80%, preferably 40-70% of the whole area of the sample-receiving surface of the wave guide. However, a more important factor in the designing of the resonators and experiments is how the sample is located in relation to the vibrational mode.

According to a preferred embodiment, capacitive electromechanical conversion of energy is utilized. By this choice, the need of piezoactive materials is avoided. The embodiments described above also provide for convenient protection of the capacitive gaps, whereby the reliability of the measurements is increased. The chips can be easily manufactured without complex starting materials or production phases using fabrication methods known per se. Capacitive actuation also provides for more flexibility in the designing of excitation and readout electronics. However, in some embodiments, the use of piezoactive transducers is justifiable.

As mentioned above, the critical parts of the sensor element can be hermetically isolated or vacuum packed. That is, the space surrounding the sample-receiving zone can be kept sealed or at underpressure until the device is used for the first time. At the time of usage, the seal (typically a distinct part of the casing of the device or a micromechanical "plug" in the device layer or the body of the sensor) is broken or removed and the sample introduced. By this embodiment, the cleanness of the sample-receiving zone can be secured and/or the introduction of the sample through the micromechanical structures can be assisted.

The input electronics of the sensor element can comprise integrated means for performing the electrical actuation, whether piezoelectric or capacitive. When using capacitive actuation, the amplitude of the voltage over the gap between the input electrode and the wave guide can be, for example, 10-100 V. The output electronics of the sensor may comprise an integrated preamplifier for detecting the resonance.

Figure 3:
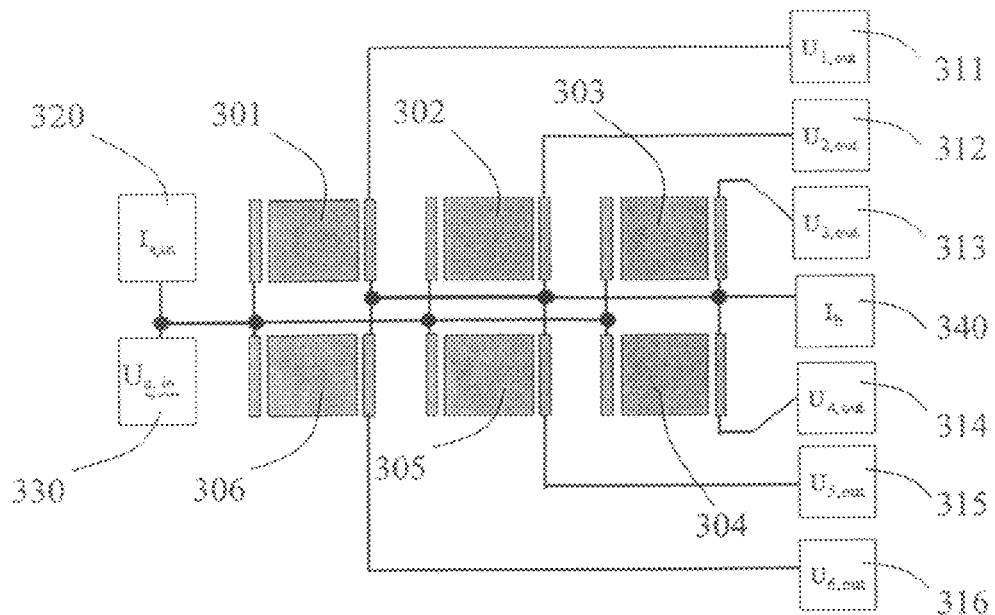
FIG. 3 shows an array of sensors according to an embodiment of the invention.

FIG. 3 shows a sensor array with six sensors as an example. Electrode $I_{a,in}$ 320 is used to drive all sensors 301-306 and electrode $U_{a,in}$ 330 is used to monitor the voltage across the sensors input terminals. A feedback electronic is used to keep the input voltage constant. The output voltages are measured via electrodes $U_{i,out}$ (i=1, 2, . . . , 6) and feedback via electrode $I_b$ zeros the output voltage. The four terminal electrode arrangement shown in FIG. 3 enables one to use capacitive contacts between the sensor elements 301-306 and readout electronics. The other possibility is to measure currents from the sensors using only one (or two) electrode(s) but in that case the mechanical resonant frequencies have to be made different in order to separate them in the frequency space. It should be noticed that if setting the resonators in parallel or in series to simplify the readout electronics impairs the resolution and should not be applied if not necessarily needed. In the case of capacitive actuation DC bias should be avoided and replaced by AC bias, if possible, in order to avoid instabilities related to the surface phenomena [Kärkkäinen1].

Figure 11:
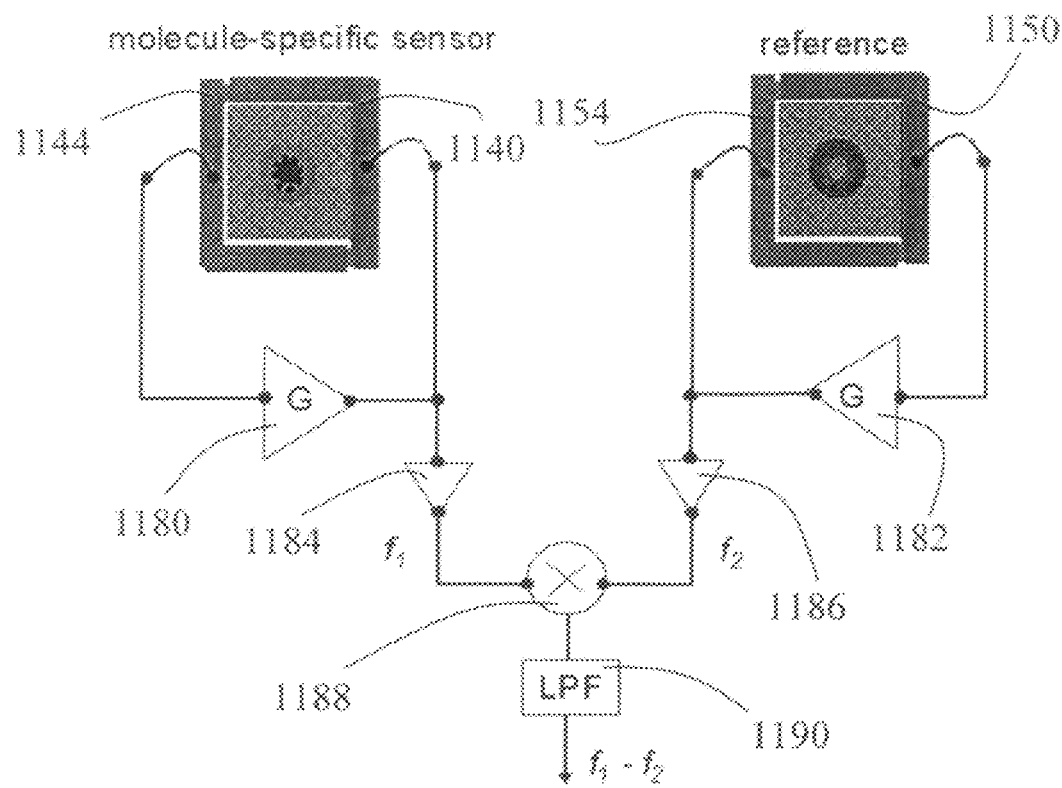
FIG. 11 illustrates a molecule-specific sensor and a reference sensor coupled for reference measurement.

FIG. 11 illustrates a measurement configuration based on two oscillators for convenient detection of the sample-induced change in the resonator eigenfrequency. In the embodiment, a molecule-specific sensor and a reference sensor are coupled in parallel and contacted to comparator circuitry 1188, 1190. The reference resonator is otherwise similar to the molecule-specific resonator, but has a non-specific sample-receiving area. Feedback circuitry 1180 is used to create the sustained oscillatory operation. The frequency difference between the two oscillators is resolved e.g. by inserting the output signals to a mixer 1188 followed by a low-pass filter 1190.

Typically the eigenfrequency of silicon micromechanical resonators exhibits a large temperature dependence (typically ~−30 ppm/K). Therefore, liquid sample insertion is expected to cause a significant temperature-change related frequency shift. However, due to the excellent thermal conductivity of silicon, the two resonators fabricated on the same chip are expected to rapidly gain thermal equilibrium with each other. By monitoring the frequency difference between the molecule-specific and reference resonators the temperature effect is canceled to the first degree.

Figure 12:
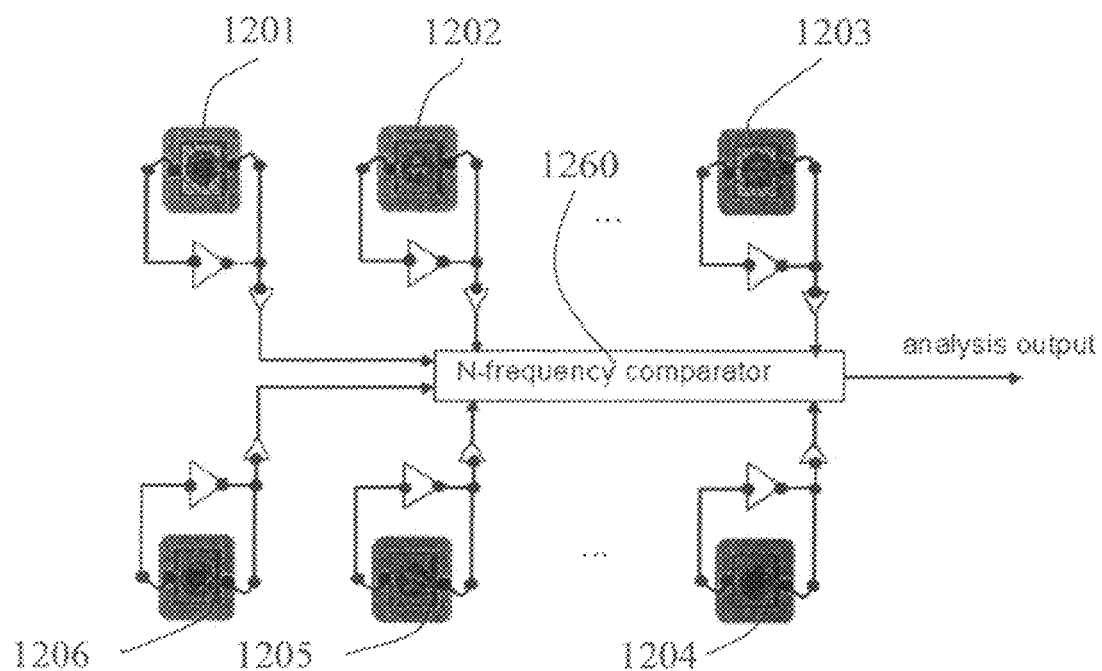
FIG. 12 illustrates a multiple-sensor configuration according to an embodiment of the invention.

Referring now to FIG. 12, as micromechanical resonator technologically is intrinsically suitable for parallelization of the devices, a multiple of resonators can be utilized for improved analysis resolution. FIG. 12 shows an example of such an arrangement having six sensor elements 1201-1206 illustrated. In a typical embodiment, half of the sensor elements are reference sensors and half of the sensors are prepared for molecule specificity using a molecule-specific layer. The sensors pairs can be coupled as described above or by a centralized comparator 1260. In another further embodiment, all of the sensors are molecule-specific. Each of the sensors or sensor pairs can be driven at the same frequency or at different frequencies. A multiple-frequency measurement can provide information on the sample not available at a single frequency.

REFERENCES

| [Vikholm1] | I. Vikholm, J. Sadowski, "Method and Biosensor for Analysis", Pat. US2003059954, FI20011877, Priority date: Sep. 24, 2001, Publication date Mar. 27, 2003. |
|---|---|
| [Vikholm 2] | I. Vikholm, Self-assembly of Antibody Fragments and Polymers onto Gold for Immunosensing. Sensors & Actuators B (2005). In Press. |
| [Vikholm 3] | I. Vikholm-Lundin, Immunosensing based on site-directed immobilisation of antibody fragments and polymer that reduce nonspecific binding, Langmuir, In press. |
| [Vikholm 4] | I. Vikholm-Lundin, W. M. Albers, A new immunosensor based on surface plasmon resonance detection of C-reactive protein. Biosensors & Bioelectronics. In press. |
| [Mattila1] | T. Mattila, J. Kiihamäki, T. Lamminmäki, O. Jaakkola, P. Rantakari, A. Oja, H. Seppä, H. Kattelus and I. Tittonen; A 12 MHz micromechanical bulk acoustic mode oscillator, Sensors and Actuators A: Physical 101, 1-2 (2002), 1-9. |
| [Kaajakari1] | V. Kaajakari, T. Mattila, J. Kiihamäki, A. Oja and H. Seppä, Square-Extensional Mode Single-Crystal Silicon Micromechanical Resonator for Low Phase Noise Oscillator Applications, IEEE Electron Device Letters 25 (2004) 173-175. |
| [Kärkkäinen 1] | A. Kärkkäinen, A. Oja, J. Kyynäräinen, H. Kuisma, H. Seppä, Stability of Electrostatic Actuation of MEMS, Physica Scripta T. Vol. T224 (2004) 193-194. |

The invention claimed is:

1. A micromechanical sensor for analyzing samples, comprising
a body,
a planar wave guide portion spaced from the body,
at least one electro-mechanical transducer element located on a lateral side of the wave guide portion for excitation of acoustic waves to the wave guide portion in response to electrical actuation, said lateral side of the wave guide portion being different from a wave guide portion side facing the body, and
a sample-receiving zone on one surface of the wave guide portion for receiving a sample, wherein the sample-receiving surface of the wave guide portion is not parallel to said lateral side of the wave guide portion, wherein the at least one of the transducer element is configured to transmit laterally oscillating longitudinal bulk acoustic waves into the wave guide portion, wherein said laterally oscillating longitudinal bulk acoustic waves oscillate parallel to the sample-receiving surface of the wave guide portion and parallel to the propagation direction of said acoustic waves, and wherein the impact of the sample on the vibrational behavior of the wave guide portion is sensed using said laterally oscillating longitudinal bulk acoustic waves.

2. A micromechanical sensor according to claim 1, further comprising at least one transducer element for converting longitudinal hulk acoustic waves carried by the wave guide portion into electrical signals.

3. A micromechanical sensor according to claim 2, wherein the transducer elements for transmitting and converting of acoustic waves comprise a single element adapted to perform the functions of transmitting and converting.

4. A micromechanical sensor according to any of claim 1, 2 or 3, wherein the body and the wave guide portion are made of a semiconductor material, such as silicon.

5. A micromechanical sensor according to claim 4, wherein the wave guide portion and at least part of the transducer elements contained in the sensor are fabricated from the semiconductor layer of a semiconductor-on-insulator structure.

6. A micromechanical sensor according to claim 5, wherein the semiconductor-on-insulator comprises a silicon semiconductor layer and the insulator layer is a buried oxide (BOX) layer, such as a $SiO_2$ layer.

7. A micromechanical sensor according to claim 5, wherein the transducer elements contained in the sensor comprise piezoelectric material, such as AlN or ZnO, arranged between the wave guide portion and the semiconductor layer of the transducer elements for piezoelectric actuation and detection of the acoustic waves.

8. A micromechanical sensor according to claim 5, wherein there is a narrow gap between the wave guide portion and the semiconductor layer of the transducer elements contained in the sensor for capacitive transduction of the acoustic waves.

9. A micromechanical sensor according to any of claims 1-3, wherein the wave guide portion is anchored to the body by at least one insulating anchor element between the body and the wave guide portion.

10. A micromechanical sensor according to claim 9, wherein the sample-receiving zone comprises a molecule-specific layer applied on the wave guide portion.

11. A micromechanical sensor according to claim 8, wherein the sample-receiving zone comprises a buffer layer arranged between the wave guide portion and the molecule-specific layer.

12. A micromechanical sensor according to claim 1, wherein at least part of the wave guide portion outside the sample-receiving zone and/or at least part of the transducer elements contained in the sensor are provided with hydrophobic coating.

13. A micromechanical sensor according to claim 12, wherein the sample-receiving zone comprises a hydrophilic surface.

14. A micromechanical sensor according to claim 13, wherein the sample-receiving zone faces away from the body.

15. A micromechanical sensor according to claim 14, wherein the body and the wave guide portion are provided with openings for introduction of samples on the sample-receiving zone from the direction of the body.

16. A micromechanical sensor according to any of the claims 1-3, wherein the sample-receiving zone faces the body and the body is provided with an opening for introduction of samples on the sample-receiving zone.

17. A micromechanical sensor according to claim 16, wherein an insulator torus is provided around the opening of the body between the body and the wave guide portion for assisting the introduction of the sample on the sample-receiving zone.

18. A micromechanical sensor according to any of claims 1-3, wherein the wave guide portion is of length $\lambda$ in a longitudinal direction and linear isolator anchor elements are provided symmetrically between the wave guide portion and the body parallel to each other and essentially at distance $\lambda/2$ from each other.

19. A micromechanical sensor according to claim 17, wherein the surfaces of the openings in thesemiconductor portions of the device and/or the insulator anchor elements are provided with hydrophilic or hydrophobic coatings for assisting the introduction of the sample on the sample-receiving zone.

20. A micromechanical sensor according to any of claims 1 to 3, wherein there are provided electrical contacts to the transducer elements contained in the sensor from a side of the sensor that is opposite to the side of sample introduction.

21. A micromechanical sensor according to any of claims 1 to 3, wherein the transducer elements contained in the sensor comprise semiconductor electrodes, which are patterned for enabling electro-mechanical transduction of longitudinal hulk acoustic waves.

22. A micromechanical sensor according to any of claims 1-3, wherein the at least one transducer element extends on two lateral sides of the wave guide portion for excitation of longitudinal bulk acoustic waves in two perpendicular directions parallel to the sample-receiving surface of the wave guide portion.

23. A micromechanical sensor according to any of claims 1-3, wherein the wave guide portion is 10-30 µm thick.

24. A micromechanical sensor according to any of claims 1-3, wherein the length of the wave guide portion in the lateral directions is 400-4000 mm.

25. A micromechanical sensor according to any of claims 1-3, wherein the sample-receiving zone is open to the exterior of the sensor.

26. A micromechanical sensor according to any of claims 1-3, wherein the sensor is packed in a hermetically sealed casing having electrical contact terminals coupled to the transducer elements contained in the sensor.

27. A micromechanical sensor according to any of claims 1-3, wherein it is incorporated in an integrated circuit (IC) structure comprising the actuation and/or readout electronics coupled to the transducer elements contained in the sensor.

28. A micromechanical sensor according to any of claims 1-3, wherein it is incorporated in an integrated circuit (IC) structure comprising an integrated reference sensor and circuitry for comparing the output signals of the sensor and the reference sensor.

29. An array of micromechanical sensors, which array comprises a body and a plurality of sensors elements, each of the sensor elements comprising a planar wave guide portion spaced from the body, at least one electro-mechanical transducer element, which are located on a lateral side of the wave guide portion for excitation of acoustic waves to the wave guide portion in response to electrical actuation and for converting acoustic waves into electrical signals, said lateral side of the wave guide portion being, different from a wave guide portion side facing the body, and a sample-receiving zone on one surface of the wave guide portion for receiving a sample, wherein the sample-receiving surface of the wave guide portion is not parallel to said lateral side of the wave guide portion, wherein the transducer element of at least one of the sensor elements is configured to transmit laterally oscillating longitudinal bulk acoustic waves into the wave guide portion, wherein said laterally oscillating longitudinal bulk acoustic waves oscillate parallel to the sample-receiving surface of the wave guide portion, and parallel to the propagation direction of said acoustic waves, and wherein the impact of the sample on the vibrational behavior of the wave guide portion is sensed using said laterally oscillating longitudinal bulk acoustic waves.

30. An array of micromechanical sensors according to claim 29, wherein at least one of the sensor elements comprises a micromechanical sensor for analyzing samples, the micromechanical sensor comprising:

a body, a planar wave guide portion spaced from the body, at least one electro-mechanical transducer element located on a lateral side of the wave guide portion for excitation of acoustic waves to the wave guide portion in response to electrical actuation, and a sample-receiving zone on one surface of the wave guide portion for receiving a sample, wherein the at least one of the transducer element is adapted to excite laterally oscillating longitudinal bulk acoustic waves to the wave guide portion.

31. An array of micromechanical sensors according to claim 29, wherein the array further comprises electrical conductors microfabricated on the array for contacting each of the transducer elements electrically outside the array element.

32. An array of micromechanical sensors according to claim 29, wherein the array comprises electrical contacts to one transducer element of each sensor element for simultaneous excitation of sensors and electrical contacts for individual reading of each sensor element.

33. An array of micromechanical sensors according to claim 29, wherein at least one of the sensor elements is a reference sensor coupled to a frequency comparator together with at least one of the longitudinal bulk acoustic wave sensors.

34. A method for sensing samples micromechanically, the method comprising the steps of introducing a sample on a sample-receiving zone of a planar micromechanical wave guide, transmitting acoustic waves into the wave guide at a lateral side of the wave guide by using a transducer by electro-mechanical coupling of the transducer and the wave guide, wherein said lateral side is not parallel to said sample-receiving zone, and converting the acoustic waves into electrical signals for wave guide for sensing the impact of the sample on the vibrational behaviour of the wave guide, wherein the step of transmitting acoustic waves transmits laterally oscillating longitudinal bulk acoustic waves into the wave guide, wherein said laterally oscillating longitudinal hulk acoustic waves oscillate parallel to the sample-receiving zone of the wave guide and parallel to the propagation direction of said acoustic waves, and said converting step senses the impact of the sample on the vibrational behavior of the wave guide using said laterally oscillating longitudinal hulk acoustic waves.

35. A method according to claim 34, wherein the method is performed using a micromechanical sensor for analyzing samples, the micromechanical sensor comprising:

a body, a planar wave guide portion spaced from the body, at least one electro-mechanical transducer element located on a lateral side of the wave guide portion for excitation of acoustic waves to the wave guide portion in response to electrical actuation, and a sample-receiving zone on one surface of the wave guide portion for receiving a sample, wherein the at least one of the transducer element is adapted to excite laterally oscillating longitudinal bulk acoustic waves to the wave guide portion.

36. A method according to claim 34, wherein the step of transmitting acoustic waves comprises transmitting longitudinal waves in two lateral directions in such a mode that the displacement of the wave guide in the vicinity of the sample-receiving zone is minimized in the direction normal to the surface of the wave guide.

37. A method according to claim 34, wherein the step of introducing the sample on the sample-receiving zone comprises conveying a liquid sample through a semiconductor layer, on which the planar micromechanical wave guide is situated.

38. A method of sensing a liquid sample comprising:

providing a semiconductor in mechanical contact with the liquid sample; and providing laterally oscillating longitudinal bulk acoustic waves to the semiconductor to excite the semiconductor, wherein said laterally oscillating longitudinal bulk acoustic waves oscillate parallel to the liquid sample surface on the semiconductor, and parallel to the propagation direction of said acoustic waves, and the liquid sample is sensed using said laterally oscillating longitudinal bulk acoustic waves.

* * * * *